United States Patent
Tsaur et al.

(10) Patent No.: US 11,471,423 B2
(45) Date of Patent: *Oct. 18, 2022

(54) MICROENVIRONMENTAL GAS PERMEABLE LAYER CAPABLE OF SUPPLYING HYDROGEN

(71) Applicant: TO2M CORPORATION, Hsinchu (TW)

(72) Inventors: Garry Tsaur, Rowland Heights, CA (US); Ting-Hua Wang, Rowland Heights, CA (US); Frank Tsaur, Rowland Heights, CA (US); Nancy Tsaur, Rowland Heights, CA (US); Emily Tsaur, Rowland Heights, CA (US)

(73) Assignee: TO2M CORPORATION, Hsinchu (TW)

( * ) Notice: Subject to any disclaimer, the term of this patent is extended or adjusted under 35 U.S.C. 154(b) by 897 days.

This patent is subject to a terminal disclaimer.

(21) Appl. No.: 16/292,932

(22) Filed: Mar. 5, 2019

(65) Prior Publication Data

US 2020/0281866 A1      Sep. 10, 2020

(51) Int. Cl.
| | |
|---|---|
| *A61K 9/70* | (2006.01) |
| *C01B 3/06* | (2006.01) |
| *C01B 3/08* | (2006.01) |
| *A61L 15/44* | (2006.01) |
| *A61K 33/00* | (2006.01) |
| *A61K 8/02* | (2006.01) |
| *A61L 15/18* | (2006.01) |
| *A61K 9/00* | (2006.01) |

(52) U.S. Cl.
CPC .......... *A61K 9/7007* (2013.01); *A61K 8/0212* (2013.01); *A61K 9/0014* (2013.01); *A61K 33/00* (2013.01); *A61L 15/18* (2013.01); *A61L 15/44* (2013.01); *C01B 3/061* (2013.01); *C01B 3/08* (2013.01)

(58) Field of Classification Search
CPC ......... C01B 3/061; C01B 3/08; A61K 9/7007; A61K 33/00; A61K 8/0212; A61K 9/0014; A61L 15/18; A61L 15/44
See application file for complete search history.

(56) References Cited

U.S. PATENT DOCUMENTS 11,096,959 B2 * 8/2021 Tsaur ..................... C01B 3/06
11,160,347 B1 * 11/2021 Tsaur ...................... A61K 8/22

OTHER PUBLICATIONS

Gregory A. DiLisi, The Hindenburg Disaster: Combining Physics and History in the Laboratory, 2017 Faculty Bibliography available at https://collected.jcu.edu/fac_bib_2017/11?utm_source=collected.jcu.edu%2Ffac_bib_2017%2F11&utm_medium=PDF&utm_campaign=PDFCoverPages (Year: 2017).*

* cited by examiner

*Primary Examiner* — Sean M Basquill
(74) *Attorney, Agent, or Firm* — Muncy, Geissler, Olds & Lowe, P.C.

(57) ABSTRACT

A gas permeable layer capable of supplying hydrogen includes a thin layer, encapsulating a hydrogen production formula. An outer side of the thin layer is airtight. An inner side is air-permeable. An inner side surface has a plurality of small holes. The thin layer can be a single layer or a composite layer. The hydrogen production formula does not dissipate. The hydrogen production formula absorbs moisture in the air or liquid water, thereby generating hydrogen. The hydrogen is released onto the skin and into the human body through the small holes. The hydrogen production formula includes metal peroxides, metal hydroxides, or metal hydrides and aluminum powder, or microsilica. The gas permeable layer can be used in sanitary products including eye masks, mouth masks, face masks, cosmetic facial masks, bras, pasties, nursing pads, sanitary napkins (towels), diapers, panty liners, wound dressing, woundplasts, bandage gauze, decubitus pads.

14 Claims, 5 Drawing Sheets

MICROENVIRONMENTAL GAS PERMEABLE LAYER CAPABLE OF SUPPLYING HYDROGEN

BACKGROUND OF THE INVENTION

Field of the Invention

The present invention provides a gas permeable layer comprising a hydrogen production formula, which belongs to the field of life care for achieving health care and disease improvement by supplying hydrogen to the skin or the human body, with the advantages of hydrogen being non-irritating, having excellent diffusion ability, and without harmful by-products of reaction.

Description of the Prior Art

Hydrogen ($H_2$) is a colorless and odorless gas. According to research reports in 1975, hydrogen can be used as an antioxidant gas to treat cancer. In 2007, Japanese scholars used hydrogen to neutralize toxic free radicals to treat cerebral ischemia-reperfusion injury. Thereafter, numerous studies have confirmed that hydrogen has therapeutic effects on a variety of diseases and injuries. As a biological anti-oxidative material, hydrogen can selectively neutralize free radicals and produce antioxidation, anti-inflammatory and anti-apoptotic effects without affecting physiological active oxygen in the body, such as superoxide anion and hydrogen peroxides, etc., indicating that hydrogen is safe for using in the human body. Another advantage of hydrogen is its powerful diffusion ability. Cell membranes and various biological barriers do not affect the diffusion and penetration of hydrogen. Hydrogen can reach any parts of the body and is considered to have therapeutic effects on common acute and chronic diseases such as apoplexy, diabetes, arteriosclerosis and Parkinson's disease.

The use of hydrogen can be carried out by inhaling hydrogen, drinking hydrogen water or injecting hydrogen brine. Inhalation of hydrogen has improvement effects on neurological and cardiovascular diseases such as apoplexy and myocardial infarction. Drinking hydrogen water has been reported to have therapeutic effects on diabetes and metabolic diseases. In addition, in animal models, drinking hydrogen water has also been proven to be capable of improving hypersensitivity diseases such as atopic dermatitis. If hydrogen brine is injected directly into the retinopathic eyeball, it can treat fundus oculi diseases. Kagoshima University in Japan and Sam Ratulangi University in Indonesia have cooperated to use high-concentration hydrogen water in combination with the anticancer drug 5-fluorouracil, using both cytological and animal models, hydrogen has been proven to be capable of promoting not only tumor cell apoptosis, but also significantly increasing the anti-tumor effect of 5-fluorouracil and prolonging the lifespan of tumor-bearing animals.

At present, the common hydrogen supply methods include hydrogen water or high-pressure hydrogen tank. Hydrogen water is prepared by fusing hydrogen into water. First, a hydrogen production machine is needed, which is bulky and requires power consumption, and the hydrogen water produced by the preparation is not easy to store. In order to supplement high-purity hydrogen, high-pressure hydrogen steel cylinder is usually used, but in addition to the problem of non-portability caused by its volume and weight, the potential safety risks of high-pressure gas steel cylinders are also of concern when using them. Since the hydrogen production machine and the high-pressure hydrogen steel cylinder are inconvenient to carry, the promotion is not easy, which makes hydrogen being limited in practical applications. Therefore, how to supply hydrogen which can be used anytime and anywhere and is easy to use is a problem to be solved by the present invention.

There are various kinds of sanitary products (including mouth masks, face masks, cosmetic facial masks, etc.) that close-fitting to the skin. Because of the direct contact with the skin, comfort and convenience of wearing is often flaunted. However, in recent years, the manufacturers in this field have also targeted to achieve synergetic efficacies and strive for improvement and breakthrough, such as the supply of oxygen and other beneficial gases to the human body through internal material reactions. However, because the gas supply comes from the internal chemical interaction between materials, in order to improve health care efficacies, often need to include more materials or a combination of more types of materials, thereby deriving the risk of material dissipation or generating unsafe by-products.

Therefore, how to provide a gas permeable layer capable of supplying hydrogen in sanitary products is an important task to be solved by the present invention.

SUMMARY OF THE INVENTION

In order to solve the aforementioned problems, the inventor of the present invention provides a gas permeable layer capable of supplying hydrogen, comprising: a thin layer, encapsulating a hydrogen production formula, wherein an outer side of the thin layer is airtight, an inner side of the thin layer is air-permeable, an inner side surface has a plurality of small holes, and the thin layer can be a single layer or a composite layer; and a hydrogen production formula, encapsulated in the thin layer, does not dissipate, absorbs moisture in the air or liquid water, thereby generating hydrogen; and the hydrogen is released into the skin and the human body through the small holes.

In order to achieve the objects of the present invention, wherein a material of the inner side of the thin layer can be a silica gel, a silicone rubber, a non-woven fabric, or a plastic gas permeable membrane.

In order to achieve the objects of the present invention, wherein a material of the outer side of the thin layer is a polypropylene, polyethylene plastic film, an aluminum film, or a composite film.

In order to achieve the objects of the present invention, wherein the hydrogen production formula can be in the form of powder or granules.

In order to achieve the objects of the present invention, wherein the hydrogen production formula comprises metal peroxides, metal hydroxides, or metal hydrides and aluminum powder or microsilica.

In order to achieve the objects of the present invention, wherein a weight ratio of metal peroxides or metal hydroxides:aluminum powder=1:100-100:1, preferably 1:10-10:1.

In order to achieve the objects of the present invention, wherein the metal peroxides are selected from a group consisting of calcium peroxide, magnesium peroxide, sodium peroxide, and potassium peroxide; the metal hydroxides are selected from a group consisting of calcium hydroxide, magnesium hydroxide, sodium hydroxide, and potassium hydroxides and the metal hydrides are selected from a group consisting of magnesium hydride, calcium hydride, and silicon hydride.

In order to achieve the objects of the present invention, wherein the hydrogen production formula can be added with a solid acid, and the solid acid is selected from a group consisting of solid citric acid, solid lactic acid, solid oxalic acid, solid hydrochloric acid, solid phytic acid, and solid silicic acid.

In order to achieve the objects of the present invention, the hydrogen production formula can further comprise superabsorbent polymers, activators or catalysts.

In order to achieve the objects of the present invention, the thin layer can further comprise oxygen and active oxygen generating units.

In order to achieve the objects of the present invention, the gas permeable layer can be used in sanitary products, and the sanitary products include eye shields, mouth masks, face masks, cosmetic facial masks, bras, pasties, nursing pads, sanitary napkins (towels), diapers, panty liners, wound dressing, woundplasts, bandage gauze, and decubitus pads.

The present invention is a gas permeable layer comprising a hydrogen production formula, which can generate a large amount of hydrogen in a short time for supplying to human skin, nostrils, mouth cavity, eyes, or other parts of the human body in contact with, and the beneficial efficacies are as follows:

1. Safe and convenient to use

It does not require steel cylinder lines or plug-in for electricity, so it is convenient and portable to carry around, and the formula is harmless and can be used by close-fitting to the human body.

2. Will not produce harmful by-products
3. Close-fitting to the skin for easy absorption
4. Hydrogen with extensive uses for body health care Excellent diffusion capacity, unlimited access points
Non-toxic, mild and safe reducing agent
Excellent anti-oxidation and anti-inflammatory effects
Improve the body flora The present invention further discloses the optimum hydrogen production formula ratio and dosage required for obtaining the optimum health care effects of the gas permeable layer, and exemplifies the application of the gas permeable layer in sanitary products, and the extended applications of the present invention.

DETAILED DESCRIPTION OF THE PREFERRED EMBODIMENTS

The present invention is exemplified by the following embodiments, but the present invention is not limited by the following embodiments. The following describes the features, applications and advantages of a gas permeable layer capable of supplying hydrogen of the present invention. Nevertheless, any equivalent implementations or modifications without departing from the technical spirit of the present invention are intended to be included in the scope of the appended claims.

Figure 1:
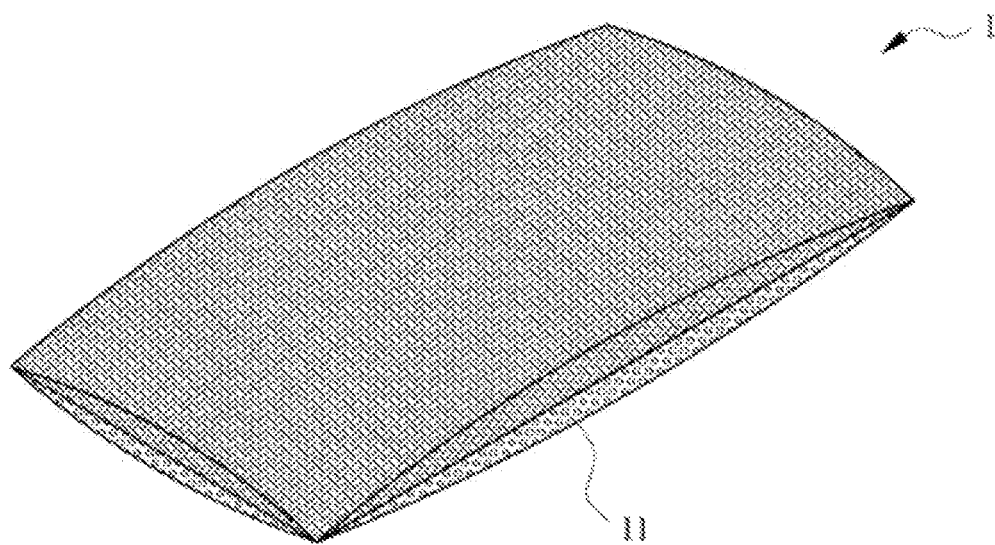
FIG. 1 is a schematic view of a gas permeable layer capable of supplying hydrogen.
Figure 2:
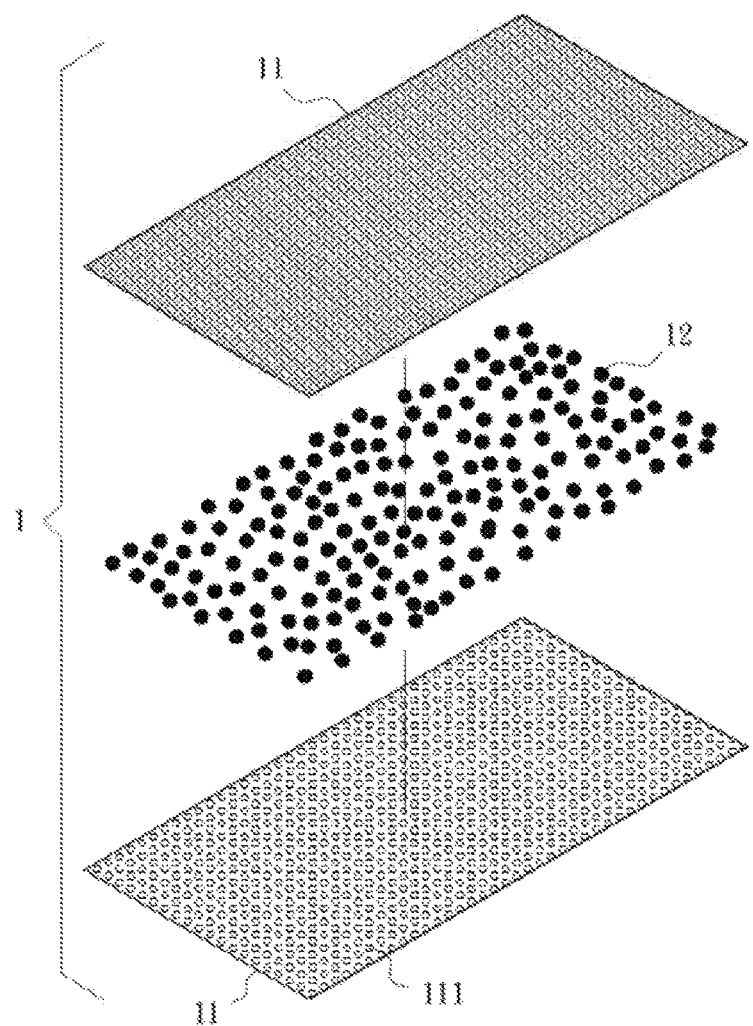
FIG. 2 is an exploded view of the gas permeable layer.
Figure 3:
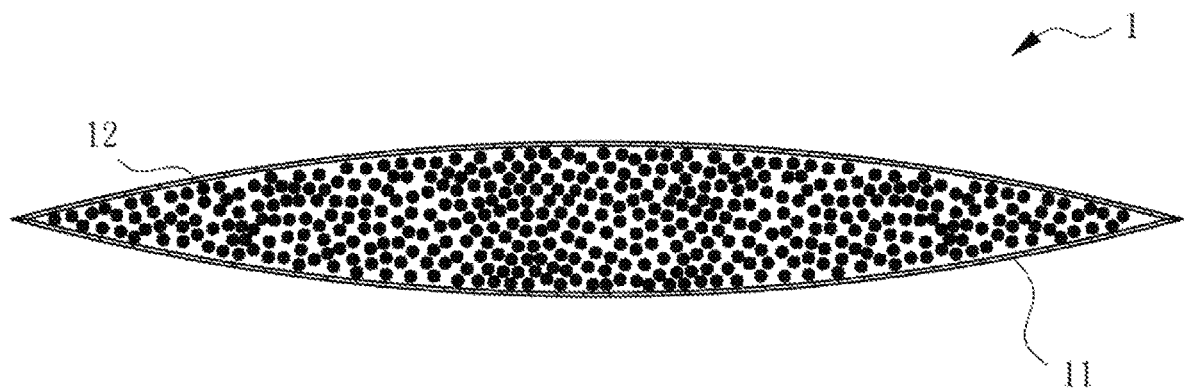
FIG. 3 is a cross-sectional view of the gas permeable layer.

As shown in FIG. 1 to FIG. 3, the present invention provides a gas permeable layer 1, comprising: a thin layer 11 encapsulating a hydrogen production formula, wherein an outer side of the thin layer 11 is airtight and an inner side of the thin layer 11 is air-permeable, an inner side surface has a plurality of small holes 111, and the thin layer 11 can be a single layer or a composite layer; and a hydrogen production formula 12, encapsulated in the thin layer 11, does not dissipate, absorbs moisture in the air or liquid water, thereby generating hydrogen. It can be seen in FIG. 2 that, through the small holes 111, the hydrogen is absorbed into the human body through skin, nostrils, mouth cavity, eyes, and other parts of the human body in contact with.

In the present invention, the hydrogen production formula 12 is encapsulated by the thin layer 11 with the outer side, which is airtight, and the inner side, which is air-permeable. The hole diameter of the small holes 111 of the inner side of the thin layer 11 is smaller than the diameter of the hydrogen production formula 12 to ensure that the hydrogen production formula 12 does not leak. The outer side of the thin layer 11 is an airtight material, and the inner side of the thin layer 11 is a skin-friendly material.

When being stored, the gas permeable layer 1 is packaged with an airtight material to ensure that moisture in the air does not react with the hydrogen production formula 12 in advance; when being used, the airtight package is torn off and applied at a desired position. By using the gas permeable layer 1, sweat and moisture can be retained from leaking through the airtight material of the outer side, so that the hydrogen production formulation 12 can react sufficiently with water and supply hydrogen to the skin.

A material of the inner side of the thin layer 11 for encapsulating the hydrogen production formula 12 can be a silica gel, a silicone rubber, a non-woven fabric, or a plastic gas permeable membrane. A material of the outer side of the thin layer 11 can be a polypropylene, polyethylene plastic film, an aluminum film, or a composite film.

The hydrogen production formula 12 can be in the form of powder or granules comprising metal peroxides, metal hydroxides, or metal hydrides and aluminum powder, or microsilica.

Wherein the metal peroxides are selected from a group consisting of calcium peroxides, magnesium peroxides, sodium peroxides, and potassium peroxides; and the metal hydroxides are selected from a group consisting of calcium hydroxides, magnesium hydroxides, sodium hydroxides, and potassium hydroxides.

The hydrogen production formula can also comprise compounds that can form metal hydroxides through moisture, such as magnesium hydrides, calcium hydrides, and silicon hydrides.

Optionally, the hydrogen production formula can be added with a solid acid that neutralizes the hydrogen production formula, so that the pH value is between 4-9 in order to avoid irritating the skin and enhance the hydrogen absorption effect. The solid acid is selected from a group composed of solid citric acid, solid lactic acid, solid oxalic acid, solid hydrochloric acid, solid phytic acid and solid silicic acid.

The following reaction provides a mechanism of the hydrogen production formula for supplying hydrogen:

In the case of peroxides, it will first react with water to form hydroxides and release oxygen, the reaction formula is:

$$2XO_2 + 2H_2O \rightarrow 2X(OH)_2 + O_2 \text{ (X is calcium, magnesium) or}$$

$$2Y_2O_2 + 2H_2O \rightarrow 4Y(OH) + O_2 \text{ (Y is sodium, potassium)}$$

Hydroxides react with the aluminum powder to form hydrogen, referring to the following reaction formulas:

$$2Al + 2H_2O + X(OH)_2 = X(AlO_2)_2 + 3H_2$$

$$2Al + 2H_2O + 2Y(OH) = 2YAlO_2 + 3H_2$$

Metal hydrides react with moisture to form hydrogen and metal hydroxides, and metal hydroxides are then reacted with water to produce hydrogen continuously.

In the aforementioned reactions, if a relatively large amount of hydrogen is to be rapidly formed, peroxides or hydroxides of an alkali metal (Group IA) (i.e. sodium or potassium) which is more active can be selected as reactants.

Through the combined applications of the aforementioned exemplary hydrogen production formula, those skilled in the art can also associate with using silicon to react with hydroxides and water to generate hydrogen, which is an equivalent implementation of the combinations of the present invention and should be included in the scope of the appended claims of the hydrogen production formula of the present invention. The reaction formulas are as follows:

$$Si + 4H_2O = H_4SiO_4 + 2H_2$$

$$H_4SiO_4 + 2NaOH = Na_2SiO_3 + 3H_2$$

In order to clarify the preferred dosage ratio, therefore, the hydrogen generation efficiency of each reactant in the range of 0.01-100 g is tested respectively. The hydrogen production formula can react to produce hydrogen when a weight ratio of metal peroxides or metal hydroxides:aluminum powder=1:100-100:1, and has the best hydrogen generation efficiency when the weight ratio is 1:10-10:1.

Figure 4:
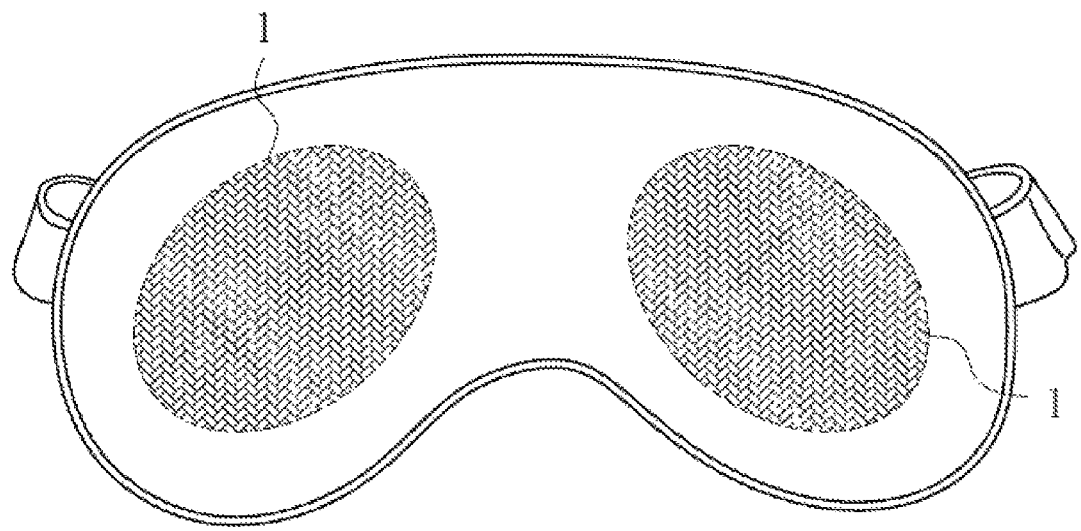
FIG. 4 is a schematic view of the gas permeable layer applied to a eye shield.
Figure 5A:
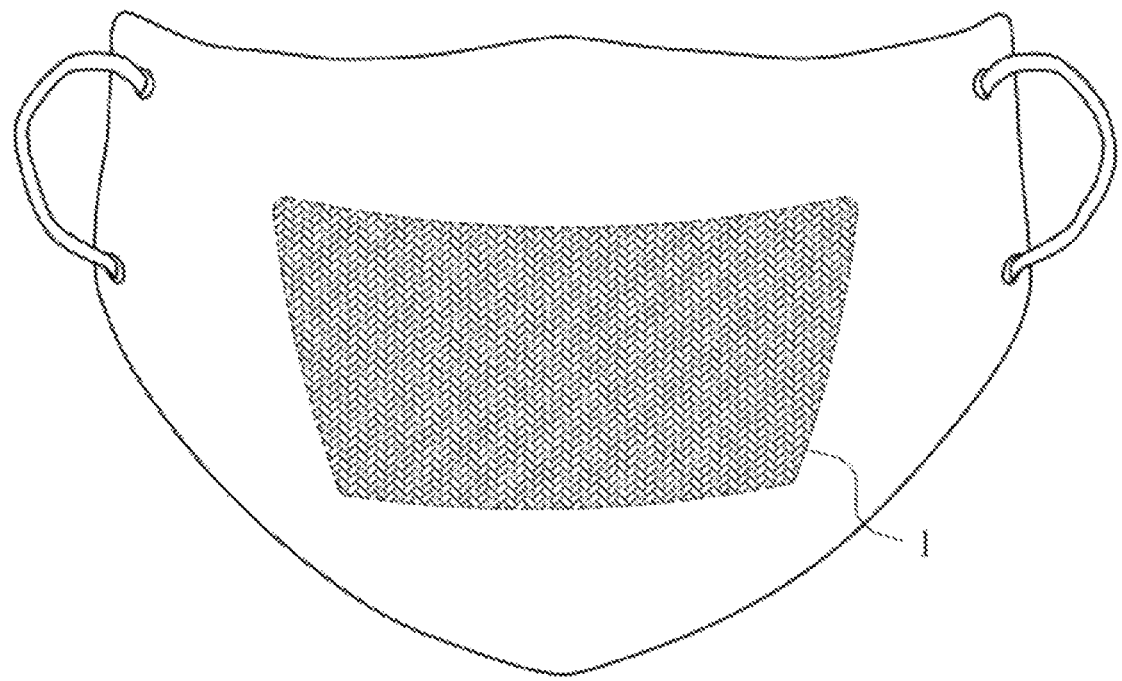
FIGS. 5A and 5B are schematic views of the gas permeable layer applied to a mouth mask.
Figure 5B:
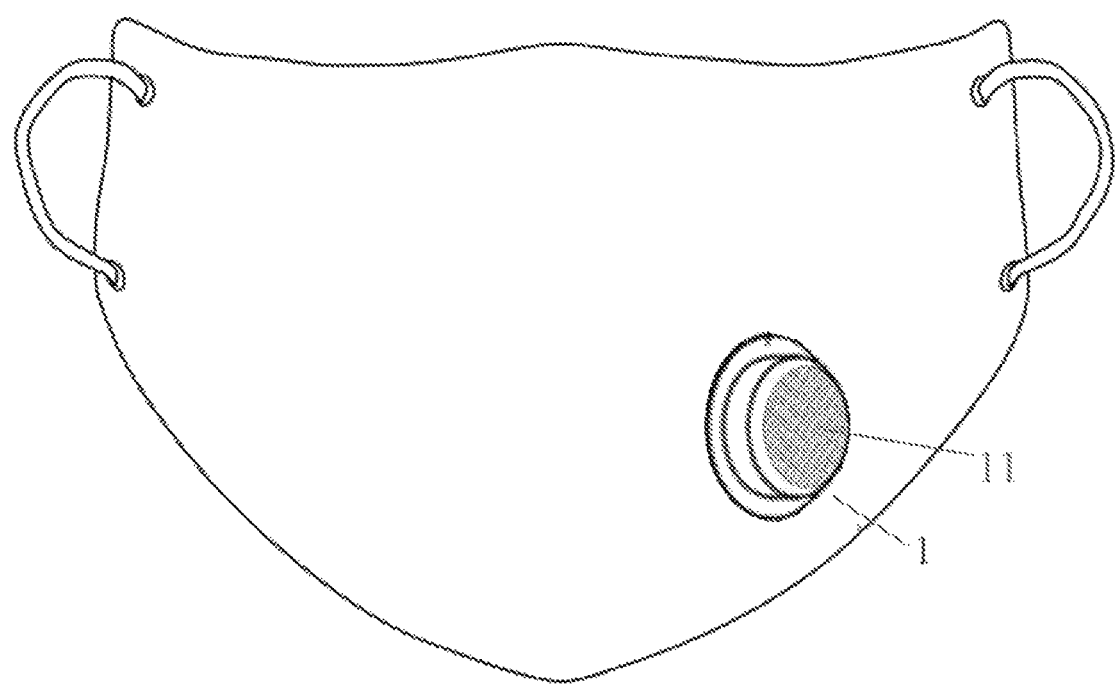
Figure 6:
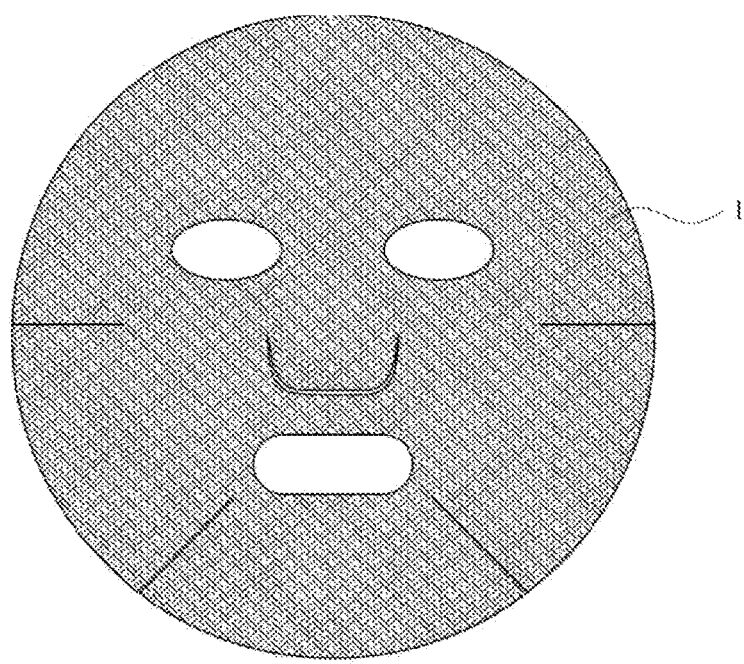
FIG. 6 is a schematic view of the gas permeable layer applied to a cosmetic facial mask.
Figure 7:
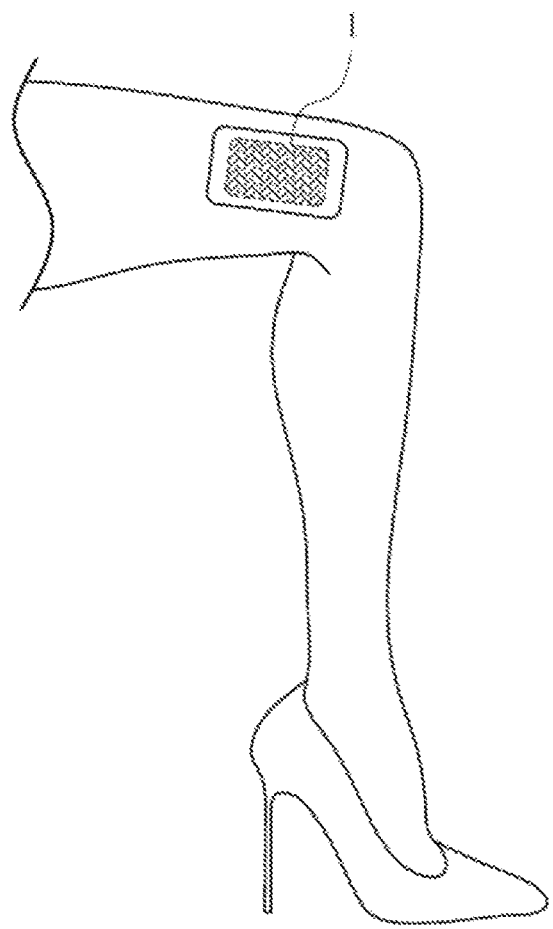
FIG. 7 is a schematic view of the gas permeable layer applied to a wound dressing.

The gas permeable layer can be used in sanitary products for close-fitting to the body. The sanitary products include but not limited to eye masks (FIG. 4), mouth masks (FIG. 5A, FIG. 5B), face masks, cosmetic facial masks (FIG. 6), bras, pasties, nursing pads, sanitary napkins (towels), diapers, panty liners, wound dressing (FIG. 7), woundplasts, bandage gauze, and decubitus pads.

In the following, testees with various related diseases and symptoms, including neurological diseases, recently treated with radiotherapy, constipation, ultraviolet injury, sore eye, eye discomfort, and trauma are recruited, distributed with sanitary products such as mouth mask, eye shield, cosmetic facial mask, or wound dressing comprising the gas permeable layer, and use for three months continuously, three times a week, two hours each time, and then fill out a questionnaire after the application to investigate. When the hydrogen production formula of the gas permeable layer is applied to the various sanitary products, the improvement efficacies on each disease and symptom is studied. The comfort of use is based on 1-10 as a scoring benchmark. The higher the score, the more remarkable the effect is. At the same time, the improvement efficacies are compared with groups of commercially available general products that do not contain gas-producing materials (hereinafter referred to as "commercially available") and those that do not contain aluminum powder (without hydrogen generation). The average results of the respective score statistics are described below. Contents of the hydrogen production formula in the gas permeable layer are adjusted according to the above preferred ratio (metal peroxides or metal hydroxides:aluminum powder=100:80-120), and according to the corresponding sanitary products.

Embodiment 1: Mouth Mask

The test groups and results are shown in Table 1 below. The peroxide is calcium peroxide and the hydroxide is calcium hydroxide. Both are 10 grams. The hydrogen production formula further contains 1 gram of aluminum powder, and a suitable amount of citric acid to produce hydrogen through skin moisture or added water.

The results show that the hydrogen production formula of the present invention can improve diseases/symptoms such as neurological diseases, side effects of radiotherapy, and constipation. These efficacies cannot be achieved either in the group of commercially available masks or in the group with generation of oxygen only (without aluminum powder). Additionally, each of the combinations of the present invention has better comfortability than the commercially available masks. When peroxides, hydroxides and solid acid are included at the same time, optimum efficacies on improving diseases and comfortability can be achieved.

TABLE 1

Efficacies on improving the various diseases and symptoms as well as comfortability of the gas permeable layer in the mouth mask

| Disease required improvement/ comfortability | Without gas production formula Commercially available | The formula of the present invention (hydrogen, by-product oxygen) | | | Only generate oxygen Peroxides, without aluminum powder |
|---|---|---|---|---|---|
| | | Peroxides + aluminum powder | Hydroxides + aluminum powder | Peroxides + hydroxides + Solid acid | |
| Neurological diseases | 1 | 5 | 6 | 8 | 2 |
| Side effects of radiotherapy | 0 | 5 | 5 | 6 | 3 |
| Constipation | 1 | 6 | 7 | 8 | 2 |
| Comfortability | 3 | 5 | 5 | 6 | 5 |

Embodiment 2: Eye Shield

The test groups and results are shown in Table 2 below. The peroxide is sodium peroxide and the hydroxide is sodium hydroxide. Both are 1 gram. The hydrogen production formula further contains 10 grams of aluminum powder, and a suitable amount of oxalic acid to produce hydrogen through added water.

The results show that the hydrogen production formula of the present invention can improve sore eye and eye diseases, and has better effects compared with the groups of commercially available eye masks and those do not contain aluminum powder (cannot generate hydrogen). Additionally, each of the combinations of the present invention has better comfortability than the commercially available eye masks, and when peroxides, hydroxides and solid acid are included at the same time, optimum efficacies on improving diseases and comfortability can be achieved.

TABLE 2

Efficacies on improving the various diseases and symptoms as well as comfortability of the gas permeable layer in the eye shield

| Disease required improvement/ comfortability | Without gas production formula Commercially available | The formula of the present invention (hydrogen, by-product oxygen) | | | Only generate oxygen Peroxides, without aluminum powder |
|---|---|---|---|---|---|
| | | Peroxides + aluminum powder | Hydroxides + aluminum powder | Peroxides + hydroxides + Solid acid | |
| Sore Eye | 3 | 7 | 8 | 9 | 4 |
| Eye diseases | 1 | 6 | 7 | 8 | 2 |
| Comfortability | 3 | 6 | 6 | 7 | 6 |

Embodiment 3: Cosmetic Facial Mask

The test groups and results are shown in Table 3 below. The peroxides are peroxide is magnesium peroxide and the hydroxide is magnesium hydroxide. Both are 12.5 grams. The aluminum powder is 6.25 grams, and the solid acid is a suitable amount of lactic acid to produce hydrogen through added water.

The results show that when compared with the groups of commercially available cosmetic facial masks and those do not contain aluminum powder (cannot generate hydrogen), the hydrogen production formula of the present invention has better efficacies on improving ultraviolet injury, side effects of radiotherapy, and neurological diseases. Additionally, each of the combinations of the present invention has better comfortability than the commercially available cosmetic facial masks, and when peroxides, hydroxides and solid acid are included at the same time, optimum efficacies on improving diseases and comfortability can be achieved.

TABLE 3

Efficacies on improving the various diseases and symptoms as well as comfortability of the gas permeable layer 1 in the cosmetic facial mask

| Disease required improvement/ comfortability | Without gas production formula Commercially available | The formula of the present invention (hydrogen, by-product oxygen) | | | Only generate oxygen Peroxides, without aluminum powder |
|---|---|---|---|---|---|
| | | Peroxides + Aluminum powder | Hydroxides + Aluminum powder | Peroxides + hydroxides + Solid acid | |
| Ultraviolet injury | 1 | 5 | 6 | 8 | 1 |
| Side effects of radiotherapy | 1 | 5 | 7 | 9 | 2 |
| Neurological diseases | 2 | 6 | 7 | 8 | 2 |
| Comfortability | 3 | 7 | 6 | 8 | 7 |

Embodiment 4: Wound Dressing

The test groups and results are shown in Table 4 below. The peroxides are peroxide is potassium peroxide, the hydroxide is potassium hydroxide. Both are 2.5 grams. The aluminum powder is 2.5 grams, and the solid acid is a suitable amount of phytic acid; the wound dressing can produce hydrogen by absorbing moisture, and moisture can be kept from being reversely released to the wound, and improved effects of supplying hydrogen, while avoiding secondary infection of the wound, can be achieved through the gas permeable layer being designed for gas circulation only.

The results show that when compared with the groups of commercially available wound dressing and those do not contain aluminum powder (cannot generate hydrogen), the hydrogen production formula of the present invention has better efficacies on improving ultraviolet injury, side effects of radiotherapy, and wound healing. Additionally, each of the combinations of the present invention has better comfortability than the commercially available wound dressing, and when peroxides, hydroxides and solid acid are included at the same time, optimum efficacies on improving diseases and comfortability can be achieved.

TABLE 4

Efficacies on improving the various diseases and symptoms as well as comfortability of the gas permeable layer in wound dressing

| Disease required improvement/ comfortability | Without gas production formula Commercially available | The formula of the present invention (hydrogen, by-product oxygen) | | | Only generate oxygen Peroxides, without aluminum powder |
|---|---|---|---|---|---|
| | | Peroxides + aluminum powder | Hydroxides + aluminum powder | Peroxides + hydroxides + Solid acid | |
| Ultraviolet injury | 1 | 6 | 5 | 8 | 2 |
| Side effects of radiotherapy | 1 | 6 | 4 | 7 | 2 |
| Wound healing | 0 | 5 | 4 | 7 | 2 |
| Comfortability | 2 | 5 | 4 | 6 | 4 |

In addition, when using a sanitary napkin (cloth) or the like being particularly required not to leak liquid, a polymer water absorbent material (i.e. superabsorbent polymer) can be added to absorb the liquid, thereby simultaneously achieving dual effects of generating hydrogen and avoiding skin infection and inflammation caused by liquid reflux.

In summary, the gas permeable layer of the present invention, regardless of the combinations of the hydrogen production formula, can be applied in sanitary products to improve neurological diseases, side effects of radiotherapy, constipation, ultraviolet injury, sore eye, eye discomfort, and wound healing. Through hydrogen with the efficacies of anti-oxidation and effects on improving flora in the body, barriers that limit functions in the conventional sanitary products can be broken through. Compared with the group that only produces oxygen (without aluminum powder), the applications of the hydrogen production formula of the present invention can achieve more excellent, wider range of body health care efficacies, and have beneficial efficacies. Because the by-products can form oxygen, the gas permeable layer has better comfortability than the commercially available products (without gas production formula), does not have the feeling of stuffy, which enhances the comfortability of use. When peroxides, hydroxides and solid acid are added at the same time, optimum efficacies on improving disease and symptoms as well as comfortability can be achieved.

In conclusion, the present invention can generate a large amount of hydrogen in a short period of time for supplying to human skin, nostrils, mouth cavity, eyes, or other parts of the human body in contact with. Compared with the general methods and apparatuses for generating hydrogen, the present invention has the advantages of not requiring steel cylinder lines, hydrogen production machine or plug-in for electricity, being convenient and portable to carry around, being harmless and can be used by close-fitting to the human skin, and being easy and convenient without generating harmful by-products.

In addition, hydrogen is also simple in structure, so it has excellent diffusion ability, and positions that can be reached are not limited. It is a non-toxic, mild and safe reducing agent, has excellent anti-oxidation effects, and has the advantage of improving the body flora. Compared with the health care purposes of the prior art sanitary products, benefits of more extensive and enhanced efficacies can be achieved.

The diseases listed in the present invention are correspondingly applied with antioxidation by hydrogen and improvement on the efficacies of flora in the body. According to the embodiments of the present invention, the gas permeable layer of the present invention can be reasonably applied to improve any other diseases caused by the lack of antioxidation by hydrogen and improvement on the efficacies of flora in the body, such as cancers, side effects of chemotherapy, metabolic diseases, immune diseases, allergies, diabetes, weight control, colitis, and the like.

In order to enhance the hydrogen generation effects, the hydrogen production formula can further comprise superabsorbent polymers, activators or catalysts depending on the situation; additionally, can also be further added with oxygen and active oxygen generating units, and adjust the ratio corresponding to different demands to achieve the desired efficacies.

The above detailed description is specifically for illustrating the feasible embodiments of the present invention, but the embodiments are not intended to limit the scope of the appended claims of the present invention, nevertheless, any equivalent implementations or modifications without departing from the technical spirit of the present invention are intended to be included in the scope of the appended claims.

The above-mentioned multiple efficacies fully meet the statutory patent requirements of novelty and non-obviousness, and therefore the application is submitted in accordance with the laws, and the Office is earnestly requested to grant the application for this utility patent to encourage invention.

What is claimed is:

1. A gas permeable layer capable of supplying hydrogen, comprising:
   a thin layer, wherein an outer side of the thin layer is airtight, an inner side of the thin layer is air-permeable, an inner side surface has a plurality of small holes, and the thin layer is a single layer or a composite layer; and
   a hydrogen production formula, encapsulated in the thin layer, wherein the hydrogen production formula does not dissipate, the hydrogen production formula absorbs moisture in the air or liquid water, thereby generates hydrogen; and
   the hydrogen is released through the small holes.

2. The gas permeable layer as claimed in claim 1, wherein a material of the inner side of the thin layer is a silica gel, a silicone rubber, a non-woven fabric, or a plastic gas permeable membrane.

3. The gas permeable layer as claimed in claim 1, wherein a material of the outer side of the thin layer is a polypropylene, polyethylene plastic film, an aluminum film, or a composite film.

4. The gas permeable layer as claimed in claim 1, wherein the hydrogen production formula is in the form of powder or granules.

5. The gas permeable layer as claimed in claim 1, wherein the hydrogen production formula comprises metal peroxides, metal hydroxides, or metal hydrides and aluminum powder or microsilica.

6. The gas permeable layer as claimed in claim 5, wherein a weight ratio of metal peroxides or metal hydroxides: aluminum powder=1:100-100:1.

7. The gas permeable layer as claimed in claim 5, wherein the metal peroxides are selected from a group consisting of calcium peroxide, magnesium peroxide, sodium peroxide, and potassium peroxide.

8. The gas permeable layer as claimed in claim 5, wherein the metal hydroxides are selected from a group consisting of calcium hydroxide, magnesium hydroxide, sodium hydroxide, and potassium hydroxide.

9. The gas permeable layer as claimed in claim 5, wherein the metal hydrides are selected from a group consisting of magnesium hydride, calcium hydride, and silicon hydride.

10. The gas permeable layer as claimed in claim 5, wherein the hydrogen production formula further comprises a solid acid, and the solid acid is selected from a group consisting of solid citric acid, solid lactic acid, solid oxalic acid, solid hydrochloric acid, solid phytic acid and solid silicic acid, in order to make the pH value between 4-9.

11. The gas permeable layer as claimed in claim 1, the hydrogen production formula further comprising superabsorbent polymers, activators or catalysts.

12. The gas permeable layer as claimed in claim 1, the thin layer further comprising oxygen and active oxygen generating units.

13. The gas permeable layer as claimed in claim 1, wherein the gas permeable layer is configured to be attached to sanitary products, and the sanitary products including eye masks, mouth masks, face masks, cosmetic facial masks, bras, pasties, nursing pads, sanitary napkins (towels), diapers, panty liners, wound dressing, woundplasts, bandage gauze, and decubitus pads.

14. The gas permeable layer as claimed in claim 5, wherein a weight ratio of metal peroxides or metal hydroxides: aluminum powder=1:10-10:1.

* * * * *